United States Patent [19]

Wolfram et al.

[11] Patent Number: 4,770,873

[45] Date of Patent: Sep. 13, 1988

[54] NEUTRALIZING COMPOSITION AND METHOD FOR HAIR WAVING AND STRAIGHTENING

[75] Inventors: Leszek J. Wolfram, Stamford; David Cohen, Milford, both of Conn.

[73] Assignee: Clairol, Incorporated, New York, N.Y.

[21] Appl. No.: 834,117

[22] Filed: Feb. 25, 1986

Related U.S. Application Data

[63] Continuation of Ser. No. 504,541, Jun. 15, 1983, abandoned.

[51] Int. Cl.$^4$ .............................................. A61K 7/09
[52] U.S. Cl. ...................................... 424/71; 424/62; 424/70
[58] Field of Search ................... 424/70, 71, 62; 132/7

[56] References Cited

U.S. PATENT DOCUMENTS

| | | | |
|---|---|---|---|
| 2,540,494 | 2/1951 | Schwarz | 132/7 |
| 2,643,375 | 6/1953 | Gant | 132/7 |
| 2,750,947 | 6/1956 | Gant | 132/7 |
| 2,782,790 | 2/1957 | Hersh et al. | 132/7 |
| 2,787,274 | 4/1957 | Gant et al. | 132/7 |
| 2,840,087 | 6/1958 | Hersh | 132/7 |
| 2,944,942 | 7/1960 | Charle | 424/72 |
| 3,143,476 | 8/1964 | Grant | 424/71 |
| 3,248,296 | 4/1966 | Steinbach et al. | 132/7 |
| 3,687,606 | 8/1972 | Shomier et al. | 8/127.51 |
| 4,426,376 | 1/1984 | Shirakura et al. | 424/71 |
| 4,597,962 | 7/1986 | Grollier et al. | 424/70 X |

FOREIGN PATENT DOCUMENTS

| | | | |
|---|---|---|---|
| 2032974 | 5/1980 | United Kingdom | 424/47 |
| 2058103 | 4/1981 | United Kingdom | 424/70 |
| 2131821 | 6/1984 | United Kingdom | |

OTHER PUBLICATIONS

Wendel et al., *Cosmetics and Toiletries*, vol. 98:103–106, May 1983.

Sagarin (Ed)., Cosmetics, Science and Technology, Interscience Publishers Inc., New York, (1957), p. 405.

*Primary Examiner*—Sam Rosen
*Attorney, Agent, or Firm*—Charles J. Zeller; Morton S. Simon

[57] ABSTRACT

A neutralizing and conditioning composition for the hair includes an oxidizing agent such as hydrogen peroxide and an amino-functional polymeric silicone additive for imparting durable conditioning benefits to the hair. A method is provided for neutralizing and conditioning hair which has been subjected to a waving or straightening treatment with keratin reducing agent by applying the new composition to the treated hair.

9 Claims, No Drawings

NEUTRALIZING COMPOSITION AND METHOD FOR HAIR WAVING AND STRAIGHTENING

This is a continuing application of application Ser. No. 504,541, dated June 15, 1983 now abandoned.

BACKGROUND OF THE INVENTION

1. Field of the Invention

This invention relates to a novel oxidant containing neutralizing composition for use in conjunction with hair waving and straightening treatments and to a process for conditioning hair which has been subjected to such treatments. More particularly, the present invention relates to a neutralizing composition containing an oxidant and an aminofunctional polymeric silicone additive for imparting durable conditioning benefits to hair which has been treated with a reducing agent to reduce the keratin bonds in the hair as well as to the hair treating process using such composition.

2. Discussion of the Prior Art

Hair waving and hair straightening processes almost invariably include two sequential steps. In the first step, the hair is softened or relaxed with a reducing lotion which allows the hair to be molded to a desired shape. In the second, a neutralizer is applied to the softened hair to harden and stabilize the newly imparted configuration.

The principal active ingredient of conventional neutralizers is an oxidizing agent, of which hydrogen peroxide is currently the most popular. The function of the oxidant is two-fold:

(i) to remove any residual excess of the reducing agent used in the softening step of the process; and (ii) to rebuild the disulfide cross-links in hair and, thus, to stabilize the new fiber shape and restore its strength and elasticity. However, as presently practiced, not all of the disulfide bonds cleaved in the softening stage of the waving or straightening process can be rebuilt, and an increase in the fiber porosity and deterioration in tactile properties of hair are frequent side effects of such processes. In many cases, the neutralizing compositions contain conditioning agents such as quaternary alkylammonium compounds, to assure smooth texture, easy combing and control of fly-away. However, the conditioning effects obtained through such additives, although beneficial, are transient and are lost after a single shampooing.

An early example of a permanent "cold" hair waving process using mercaptan reducing agents is disclosed by Schwarz in U.S. Pat. No. 2,540,494. Schwarz teaches that the oxidizing agents in the neutralizing or setting solution used to restore the disulfide bonds can consist of any of the typical oxidizing compounds which are nonharmful when applied to hair on the human head and are non-toxic and exemplifies such oxidizing agents with salts of oxidizing acids, e.g. bromates and iodates of sodium and potassium; hydrogen peroxide and its salts, such as ammonium sulfate peroxide, urea peroxide and pyrophosphate peroxides, carbonate peroxides and perborates of sodium and potassium, as well as metal salt peroxides, salts of persulfuric acid and organic peroxides and substituted peroxides. It is also known from Schwarz that the setting "neutralizing" solution can include at least one acidifying reagent which may be provided by an acidic oxidizing agent such as potassium bromate or potassium iodate, or any acid capable of establishing a pH range in the neutralizing solution of from 2 to 4. This patent lists as exemplary acids mono- or poly-carboxylic organic acids such as malonic, succinic, maleic, acetic, propionic, butyric and crotonic; organic acids with hydroxy groups, e.g. lactic, citric, tartaric, malic and glycollic; inorganic acids such as sulfuric, hydrochloric and phosphoric; and acid salts including potassium or sodium, acid tartrate, citrate, or phthalate. It is further taught that a buffering salt can be employed to stabilize the pH, for example, sodium acetate and acetic acid at a 2:1 ratio to provide a pH of about 3.

It is also known in the art to use various types of silicon containing polymers such as polysiloxanes for conditioning hair in permanent waving processes. For instance, Steinbach, et al in U.S. Pat. No. 3,248,296 disclose various epoxy organosiloxanes to provide an elastic coating to protect hair which has been subjected to a sequential reducing treatment and oxidizing treatment from penetration by water without making the hairs stick to each other. In this case, the epoxy organosiloxanes are applied after the neutralization step with hydrogen peroxide oxidizing agent.

Shomier, et al in U.S. Pat. No. 3,687,606, which is described as an improvement of the aforementioned Steinbach, et al patent, explains that the epoxy organosiloxanes function by having the epoxy groups react with the substance of the hair while the organopolysiloxane moiety imparts water repellancy. However, the prior compounds are noted to have the disadvantages of presenting an oily gloss to the hair and not being water soluble. Accordingly, Shomier, et al provide epoxy silanes as treating agents which are applied before the neutralizing treatment with the peroxide oxidizing agent but after the reducing treatment with, for example, a thioglycollic aqid reducing agent.

In U.S. Pat. No. 2,944,942 to Charle, methylsilyl mercaptoacetates are used as permanent wave treating agents for single step use. These compounds dissociate into a mercapto reducing agent while generating polymers of silanols to protect the hair and facilitate combing. This patent does not talk about any subsequent treatment such as fixing by peroxides and it is not clear whether any such treatment would be required.

Other hot and cold waving and straightening hair treating compositions, which may or may not be used in conjunction with reducing and/or oxidizing agents, in which various types of siloxane polymers are used to form protective film coatings on individual hairs are described in, for example, U.S. Pat. Nos. 2,643,375, 2,750,947, 2,782,796, 2,787,274, and 2,840,087. U.S. Pat. No. 3,143,476 to Grant discloses a cold wave neutralizing composition and process in which sodium and potassium bromates are used as the neutralizing agents in the presence of ferrous, ferric and copper ions which function as catalysts to increase the reaction rate of the neutralizing agents.

There still remains a need for neutralizing compositions for use in a cold permanent waving or straightening hair treating process which provides durable conditioning benefits, i.e. stable to repeated shampooings. There is additionally a need in the art for such neutralizing compositions which can be applied to either waved or straightened hair which significantly reduces drying time and which bring about a drastic decrease in the hair fiber porosity resulting from excessive destruction of the hair bonds while bringing about such additional beneficial results as smooth texture, easy combing and control of fly-away and which also reduces drying time.

SUMMARY OF THE INVENTION

It is an object of the present invention to provide a neutralizing composition for hair waving and straightening which provides durable conditioning benefits, namely stability to repeated shampooings.

It is another object of the invention to provide a composition capable of neutralizing excess reducing agent and to rebuild the disulfide cross-links in hair resulting from a hair softening step which allows the hair to be dried in a reduced amount of time and which imparts improved texture, combability and reduced fly-away to the so-treated hair.

It is another object of the present invention to provide a process for simultaneously neutralizing and conditioning hair on a human head which has been subjected to exposure to a keratin reducing agent such as thioglycollic acid.

These and other objects of the present invention which will become apparent from the following detailed description of preferred embodiments are accomplished by a neutralizing and conditioning composition for hair in the form of an aqueous solution of an oxidizing agent and emulsified in the aqueous composition an amino-functional silicone polymer conditioning agent. The amino-functional silicone polymer is selected from the class of silicone polymers having amino functional groups and in particular, the silicone polymers include repeating structural units of the formula (I):

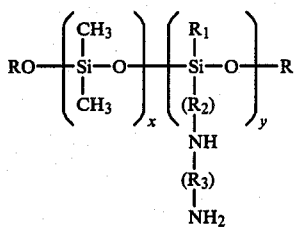

wherein

R represents a hydrogen atom or trimethylsilyl, $R_1$ represents hydroxyl or methyl, $R_2$ represents an alkylene group of from 1 to 6 carbon atoms, $R_3$ represents an alkylene group of from 1 to 4 carbon atoms, x is a positive number of at least 4, y is a positive number of at least 2, and the sum of x and y is such that the silicone polymer has a molecular weight of from about 5,000 to about 100,000.

The present invention also provides a process for neutralizing and conditioning keratinic fibers such as human hair which has been subjected to a reducing treatment to reduce the disulfide bonds in the keratinic fibers by applying to the reduced fibers an aqueous solution of an oxidizing agent and emulsified in the solution an amino-functional silicone polymer conditioning agent which includes the repeating structural units of the formula (I).

DETAILED DESCRIPTION OF THE INVENTION AND PREFERRED EMBODIMENTS

The composition and process of the present invention are generally applicable to any of the conventional reducing agents and reducing compositions as well as to any of the conventional active neutralizing agents. The reducing agents and reducing agent compositions which are generally based on thioglycollic acid or thioglycollic acid salts are wellknown in the art and do not, per se, form any part of the present invention. In addition to the thioglycollic acid class of reducing agents other hair treating agents for imparting shapability to hair, such as, for example, the "hair waving mercaptans" (see U.S. Pat. No. 2,540,494); alkali relaxer compositions, sulfite based systems, and the like can also be effectively neutralized by the neutralizing and conditioning composition of this invention.

In neutralizing and conditioning compositions of this invention, hydrogen peroxide is the preferred neutralizing/oxidizing agent. However, other neutralizing agents including inorganic and organic peroxides and peroxide salts, perborates, bromates and the like, can also be used. In addition, neutralization can also be provided in the case of the alkali reducer compositions by acidic neutralizing agents, including HCl and other inorganic mineral acids in appropriate dilute concentrations. The amount of oxidizing agent can be within the ranges normally utilized for neutralizer compositions and will depend, for example, upon the type of oxidizing agent, the amount employed and the type of the reducing agent, etc. Generally, the amount of the oxidizing agent, will range from about 0.5% to about 10% by weight, preferably from about 1% to about 4% by weight.

For optimum results, the neutralizing and conditioning compositions of the invention should have an acidic pH in the range of about 2 to 5, preferably about 2.5 to 4.5. Any of the acids conventionally used in hair neutralizing and oxidizing compositions such as those disclosed in the aforementioned Schwarz U.S. Pat. No. 2,540,494 can be used in the present invention. It is most preferred, however, to use a buffered acidified solution so that, for example, the generally present high natural alkalinity of hair will not substantially increase the pH of the invention compositions. Although optional, the use of the buffer is also preferred so that the amount of damage to the hair from harsh waving chemicals will be minimized. Any acid and buffer system capable of maintaining a pH in the desired pH range of 2 to 5 can be used in the composition of this invention. Especially good results have been obtained using phosphoric acid as the acidifying agent and a citric acid/citrate ion buffer system. However, other acids and buffer systems can also be used so long as the pH can be maintained in the range of 2 to 5. Preferably, the buffering agent is provided separately from the remaining ingredients of the composition to avoid breaking the silicone emulsion in the, e.g. peroxide, neutralizing agent upon standing on the shelf for a prolonged time due to the high acid capacity generated by the buffer, and is combined with the other ingredients just prior to use.

The oxidizing agent, e.g. hydrogen peroxide, is the main active ingredient of the composition and functions to remove any residual excess of the reducing agent or alkali used in the softening step of the waving or straightening process while additionally restoring the keratin disulfide bonds cleaved in the previous reducing step.

The other critical component of the compositions of this invention is the silicone polymer conditioning agent. These are amino-functional silicone polymers which can be represented by the following formula (I):

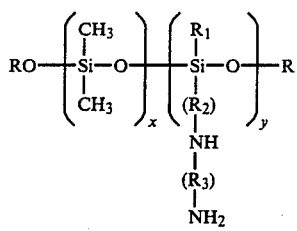

wherein
R represents a hydrogen atom or trimethylsilyl,
$R_1$ represents hydroxyl or methyl,
$R_2$ represents a divalent alkylene group of from 1 to 6 carbon atoms, preferably 2 to 4 carbon atoms, which may be straight or branched;
$R_3$ represents a divalent alkylene group of from 1 to 4 carbon atoms, preferably 2 to 3 carbon atoms, which may be straight or branched;
x is a positive number of at least 4; and
y is a positive number of at least 2.

One such suitable amino-functional silicone polymer has the common name amodimethicone which is a cationic polymer of the formula (1) wherein R is hydrogen, $R_1$ is —$CH_3$, $R_2$ is $-(CH_2)_3-$ and $R_3$ is $-(CH_2)_2-$. Amodimethicone is commercially available in the form of its aqueous emulsion from Dow Corning under the designations Dow Corning 929 Emulsion and Silicone 929 Cationic Emulsion.

The amount of the silicone polymer is generally in the range of from about 0.1 to 10% by weight, preferably from about 1 to 2% by weight of the composition. At amounts below about 0.1%, the conditioning benefits are insufficient while at amounts above about 10%, no additional benefits are observed and stable emulsions are more difficult to prepare.

Any emulsifying agents which can maintain a stable emulsion and which are compatible with the remaining ingredients can be used in the neutralizing and conditioning compositions of this invention. Preferably cationic type emulsifying agents will be used with the cationic silicone polymers (R=H) and nonionic type emulsifying agents will be used with the nonionic silicone polymers (R=trimethylsilyl). Generally, these amino-functional silicone polymers are commercially available in the form of emulsions and can be used as such in the compositions of this invention without separate addition of an emulsifying agent. For instance, Dow Corning Emulsion 929, which is an emulsion of the cationic silicone polymer, amodimethicone, includes a mixture of a cationic emulsifier (tallow trimonium chloride) and a nonionic emulsifier (an ethoxylated phenol). The Dow Corning Emulsion X2-7224, which, according to its manufacturer, is an emulsion containing about 35% by weight of a nonionic silicone polymer of formula I in which R is trimethylsilyl, $R_1$ is methyl, $R_2$ is isobutyl

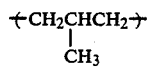

and $R_3$ is ethyl $-(CH_2CH_2)-$, includes a mixture of nonionic emulsifiers, namely about 3% by weight of an ethoxylated alcohol (Triton X405, a product of Rohm and Haas) and about 3% by weight of an ethoxylated phenol (Tergitol TMN-6, a product of Union Carbide).

Generally, any of the conventional emulsifying agents typically used in hair treating compositions can be used in the compositions of this invention. Representative nonionic emulsifiers include, for example, polyethoxylated or polyglycerolated alcohols, alkylphenols or fatty acids having a linear chain of 8 to 18 carbon atoms, and generally 2 to 30 moles of ethylene oxide, ethylene oxide/propylene oxide copolymers, fatty alcohols, condensates of ethylene or propylene oxide with fatty alcohols, polyethoxylated fatty amides, polyethoxylated fatty amines, ethanolamides, glycol esters of fatty acids, sorbitol esters of fatty acids and saccharose esters of fatty acids.

Representative cationic emulsifiers include, for example, quaternary ammonium, morpholinium, and pyridinium compounds.

The amount of the emulsifying agent or agents is not particularly critical so long as the silicone polymer is maintained in the emulsified state after blending with the oxidizing agent and other components of the compositions. Generally, amounts of the emulsifier or emulsifiers in the range of from about 2 to about 20%, preferably from about 8 to about 18%, by weight of the silicone polymer are satisfactory.

The silicone polymer, if it is not provided in an emulsified state, is preferably emulsified with one or more emulsifying agents before being mixed with the aqueous acidic solution of the oxidizing agent. The mixing of the emulsifying agent(s) with the silicone polymer, if necessary, and the blending of the emulsified silicone polymer with the aqueous acidic solution of the oxidizing agent can be simply performed by mixing the ingredients in any conventional mixing or blending apparatus at room temperature or at slightly elevated temperature. Of course, mixing speeds, shear rate, etc., should not be such as to cause breaking of the emulsion.

Other conventional additives, such as, for example, perfumes and other fragrances, thickening agents, surface active agents, other conditioning agents, germicides, bacteriocides, and the like, can be added to the compositions in amounts which do not interfere with the activity of the oxidizing agent or silicone polymer and which do not interfere with the stability of the emulsion.

The buffering agent can be added to the compositions at any time, however, it is usually preferred to package the buffering agent separately from the other components of the compositions with instructions to the user to mix the two packages just prior to use.

Although not wishing to be bound by any particular theory to the mechanism by which the silicone polymers exhibit their beneficial properties, it is presumed that the silicone polymers form a stable, adherent, mechanically strong, and abrasion resistant film on the individual hairs which eases combability and facilitates drying of the hair. The latter phenomenon may be due to the low surface tension properties of the silicone polymers which results in formation of thin water films which can be more easily evaporated from the treated hair.

As previously described, the neutralizing and conditioning compositions of this invention can be used with substantially any hair treating composition which accomplishes its waving straightening function by reduction of the keratinic disulfide bonds. The following is representative of a typical relaxer composition:

| Ingredient | Concentration (Weight %) |
| --- | --- |
| Petrolatum | 24.00 |
| Mineral Oil | 16.00 |
| Polawax (nonionic emulsifying wax) | 8.00 |
| Solulan 25 (ethoxylated lanolin alcohol) | 3.00 |
| Propylene glycol | 2.50 |
| Sodium hydroxide | 1.75 |
| Cetyl alcohol | 1.25 |
| Fragrance | 0.50 |
| Water q.s. to | 100.00 |

A conventional thioglycolate waving composition is provided by the following lotion formulation:

| Ingredient | Concentration (Weight %) |
| --- | --- |
| Ammonium thioglycolate | 5.1 |
| Monoethanolamine | 2.5 |
| Brij 35 (polyoxyethylene lauryl ether) | 1.2 |
| Fragrance | 1.0 |
| Opacifier | 1.0 |
| Water q.s. to | 100.0 |

The invention will now be described by way of the following illustrative but non-limitative examples in which all "parts" and percentages are on a weight basis unless otherwise noted.

EXAMPLE I

Three brown Caucasian hair tresses, 2 g each, are wound on ½ inch rods and are saturated with a conventional thioglycolate lotion (0.6 M ammonium thioglycolate, pH 9.2). After 20 minutes, the waving lotion is rinsed off and the tresses, while still on the rods, are treated in the following manner:

Tress #1 is saturated for 5 min. with 1.2% $H_2O_2$ adjusted to pH 4 with phosphoric acid;

Tress #2 is saturated for 5 min. with 1.2% $H_2O_2$ containing 1.5% amodimethicone adjusted to pH 4 with phosphoric acid;

Tress #3 is saturated for 5 min. with 1.2% $H_2O_2$ containing 1.5% amodimethicone adjusted to pH 3 with phosphoric acid and buffered with citric acid (0.25 M). After 5 minutes, the rods are removed, the peroxide solutions are worked into loose hair coils, left for an additional 3 minutes and rinsed off under running tap water. The tresses are then wet combed using a strain gauge comb and the work of combing is recorded. The following results are obtained:

| Tress # | Work of Combing (gcm) |
| --- | --- |
| 1 | 795 |
| 2 | 137 |
| 3 | 132 |

After combing, the tresses are re-immersed in water, removed and freely hung to dry. Their weights are recorded immediately after removal from water and after drying. The water contents of tresses as calculated from the difference in dry and wet weights are as follows:

| Tress # | Water pick-up (g/1 g of hair) |
| --- | --- |
| 1 | 2.5 |
| 2 | 1.5 |
| 3 | 1.6 |

The amount of water held by the hair after centrifuging (liquid retention of porosity index) is also measured, yielding the following results:

| Tress # | Liquid Retention (%) |
| --- | --- |
| 1 | 42.5 |
| 2 | 41.3 |
| 3 | 37.5 |

Finally, the tresses are shampooed twice and their wet combing is re-determined. The values of combing work are as follows:

| Tress # | Work of Combing (gcm) |
| --- | --- |
| 1 | 764 |
| 2 | 180 |
| 3 | 133 |

EXAMPLE II

In order to demonstrate the faster rate of hair drying at the completion of the waving (or straightening) procedure, the following experiment is carried out.

A group of four hair tresses (intact DeMeo brown hair, 2 g per tress) is waved for 15 minutes at 35° C. using a conventional waving lotion. The hair is then rinsed and two tresses are neutralized with a conventional neutralizer (2.0% $H_2O_2$) while the other two are neutralized with a combination of $H_2O_2$ (2.0%) and amodimethicone (2.0%). In both cases, the neutralization is carried out for 10 minutes, after which time the tresses are rinsed and each of them is attached to a stress gauge allowing for accurate weight determination. The weighing is continuously monitored for a period of 45 minutes. The data of Table I show the weight changes (mean average of 2) at selected time intervals. The lower the water content of hair the faster it dries.

TABLE I

| Neutralization System | Water content of hair (g $H_2O$/g of hair) following neutralization Time (min) | | | | | | |
| --- | --- | --- | --- | --- | --- | --- | --- |
| | 0 | 5 | 10 | 15 | 20 | 30 | 45 |
| $H_2O_2$ only | 2.03 | 1.59 | 1.39 | 1.23 | 1.09 | .86 | .55 |
| $H_2O_2$ + silicone | 1.51 | 1.10 | .95 | .84 | .74 | .57 | .35 |

EXAMPLE III

A composition according to the invention is prepared by adding two thickening agents (Igepol CO 430 and Igepol CO 630) and an additional emulsifying agent, cetyl alcohol:

| Component | Weight % |
| --- | --- |
| Hydrogen peroxide | 2.0 |
| Cetyl Alcohol | 0.2 |
| Igepol CO 430 | 4.0 |
| Igepol CO 630 | 4.0 |
| Phosphoric Acid | 0.03 |
| Dow Corning Emulsion 929 | 4.00 |

| Component | Weight % |
| --- | --- |
| Water | 85.77 |

A stable thickened composition is obtained.

What we claim is:

1. An oxidizing and conditioning composition for hair comprising an aqueous solution of an oxidizing agent, and an aqueous emulsion of a silicone polymer of the formula

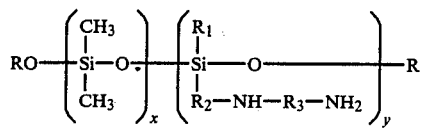

wherein

R represents hydrogen or trimethylsilyl, $R_1$ represents hydroxyl or methyl, $R_2$ represents alkylene of from 1 to 6 carbon atoms, $R_3$ represents alkylene of from 1 to 4 carbon atoms, x is a number of at least 4, y is a number of at least 2, and the sum of x+y is such that the silicone polymer has a molecular weight in the range of from about 5000 to about 100,000, said composition having a pH in the range of from about 2.0 to about 5.0.

2. The composition of claim 1 where the amount of the silicone polymer is from about 1 to 2% by weight.

3. The composition of claim 1 wherein R is hydrogen, $R_1$ represents hydroxyl, $R_2$ represents $-(CH_2)_3$ and $R_3$ represents $-(CH_2)_2$.

4. The composition of claim 1 which further comprises a buffering agent to maintain the pH of the composition in the range of from about 2.0 to 5.0.

5. The composition of claim 4 wherein the buffering agent is citric acid/citrate salt and wherein the composition is acidified to a pH of about 3.0 with phosphoric acid.

6. A method for neutralizing and conditioning hair which has been treated with a waving or straightening composition with a reducing agent capable of reducing keratinic disulfide bonds which comprises applying to the treated hair a composition containing an effective amount of oxidizing and conditioning composition of claim 1.

7. The method of claim 6 which further comprises mixing the oxidizing and conditioning composition with a buffering agent capable of maintaining the pH of the oxidizing and conditioning composition within said pH range of 2.0 to 5.0 in the presence of any residual alkalinity in the treated hair, said mixing performed just prior to applying the composition to the treated hair.

8. The composition of claim 1 wherein the oxidizing agent is hydrogen peroxide.

9. The composition of claim 2 wherein the oxidizing agent is hydrogen peroxide.

* * * * *

UNITED STATES PATENT AND TRADEMARK OFFICE
CERTIFICATE OF CORRECTION

PATENT NO. : 4,770,873
DATED : September 13, 1988
INVENTOR(S) : Leszek J. Wolfram; David Cohen It is certified that error appears in the above-identified patent and that said Letters Patent is hereby corrected as shown below:

Column 9, line 10, claim 1, after "polymer" insert --, which is from about 0.1 to about 10% by weight based on the total composition, and being--.

Signed and Sealed this

Twenty-seventh Day of December, 1994

Attest:

BRUCE LEHMAN

Attesting Officer

Commissioner of Patents and Trademarks